US012137893B2

(12) United States Patent
Kim

(10) Patent No.: US 12,137,893 B2
(45) Date of Patent: Nov. 12, 2024

(54) PERFORATOR-INTEGRAL SUTURE ANCHOR DEVICE

(71) Applicant: Korea University Research and Business Foundation, Seoul (KR)

(72) Inventor: Soung-Yon Kim, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 635 days.

(21) Appl. No.: 17/418,953

(22) PCT Filed: Nov. 12, 2019

(86) PCT No.: PCT/KR2019/015320
§ 371 (c)(1),
(2) Date: Jun. 28, 2021

(87) PCT Pub. No.: WO2020/138711
PCT Pub. Date: Jul. 2, 2020

(65) Prior Publication Data
US 2022/0117595 A1 Apr. 21, 2022

(30) Foreign Application Priority Data
Dec. 27, 2018 (KR) .......................... 10-2018-0170260

(51) Int. Cl.
*A61B 17/04* (2006.01)
(52) U.S. Cl.
CPC .. *A61B 17/0401* (2013.01); *A61B 2017/0409* (2013.01); *A61B 2017/0414* (2013.01); *A61B 2017/044* (2013.01)

(58) Field of Classification Search
CPC ........ A61B 17/0401; A61B 2017/0409; A61B 2017/0414; A61B 2017/044;
(Continued)

(56) References Cited

FOREIGN PATENT DOCUMENTS

CN     107361805 A     11/2017
EP     3228278 A1 * 10/2017     ......... A61B 17/0401
(Continued)

OTHER PUBLICATIONS

International Search Report issued on Feb. 25, 2020 for corresponding international application No. PCT/KR2019/015320.
(Continued)

*Primary Examiner* — Brooke Labranche
*Assistant Examiner* — Nasheha Baset
(74) *Attorney, Agent, or Firm* — Hauptman Ham, LLP

(57) ABSTRACT

A perforator-integral suture anchor device is proposed. More specifically, it simultaneously inserts and fixes the suture anchor into the bone while the pilot hole in the bone is forming when an anchor driver is pressed and rotated. The perforator-integral suture anchor device includes the suture anchor having threads formed on an outer circumferential surface thereof, and the anchor driver capable of pressing and rotating the suture anchor, wherein the anchor driver includes a plurality of guide arms protruding forward by being spaced apart from each other relative to a central axis of the anchor driver, and a perforating tip formed at a front end of each of the guide arms, and the suture anchor includes a plurality of female coupling grooves recessed on an outer surface of the suture anchor in a longitudinal direction thereof and allowing the suture anchor to be coupled to the plurality of guide arms.

7 Claims, 5 Drawing Sheets

(58) Field of Classification Search
CPC . A61B 17/8883; A61B 17/863; A61B 17/864; A61B 17/8645; A61B 2017/00004; A61B 17/1604; A61B 2017/0464; A61B 2017/0441; A61B 2017/0443; A61F 2/0811; A61F 2002/0841; A61F 2002/0858; A61L 31/06; A61L 17/10
See application file for complete search history.

(56) References Cited

FOREIGN PATENT DOCUMENTS

| | | |
|---|---|---|
| KR | 10-2013-0041957 A | 4/2013 |
| KR | 10-2014-0056983 A | 5/2014 |
| KR | 10-2015-0128684 A | 11/2015 |
| KR | 10-2016-0110599 A | 9/2016 |
| KR | 10-2017-0005230 A | 1/2017 |

OTHER PUBLICATIONS

Written Opinion issued for corresponding International Patent Application No. PCT/KR2019/015320 on Feb. 25, 2020.

* cited by examiner

PERFORATOR-INTEGRAL SUTURE ANCHOR DEVICE

CROSS-REFERENCE TO RELATED APPLICATION

The present application is a national stage filing under 35 U.S.C. § 371 of PCT application number PCT/KR2019/015320 filed on Nov. 12, 2019 which is based upon and claims the benefit of priorities to Korean Patent Application No. 10-2018-0170260, filed on Dec. 27, 2018, in the Korean Intellectual Property Office. Both of the aforementioned applications are hereby incorporated by reference in their entireties.

TECHNICAL FIELD

The present disclosure generally relates to a perforator-integral suture anchor device. More particularly, the present disclosure relates to a perforator-integral suture anchor device, which forms a pilot hole in a bone when an anchor driver is pressed and rotated, and simultaneously inserts and fixes a suture anchor into the bone while the pilot hole is formed.

BACKGROUND ART

Tear of the tendon tissue from the original bone attachment site due to the degeneration or injury mostly requires surgical repair. The torn tendon tissue is fixed to the original bone attachment site using a suture anchor system during arthroscopic surgery.

The existing threaded suture anchor devices require the awl, dilator, or tapper for the pilot hole preparation before the suture anchor insertion. They are configured as a combination of a suture anchor and an anchor driver necessary for pressing and rotating the suture anchor.

For the process of inserting and fixing such the threaded suture anchor into the bone, the pilot hole is first prepared in the bone using the awl, dilator, or tapper, which is a separate instrument, and then the threaded suture anchor is inserted into the prepared pilot hole through the adjusting process of the suture anchor position aligning over the position and axis of the prepared pilot hole.

The suture anchor made of bioabsorbable or biocomposite material, which is currently preferred to use, is vulnerable to damage or breakage during suture anchor insertion into the bone because they are more fragile than metal or PEEK (polyetheretherketone) ones. Therefore, preparation of the pilot hole and protecting the anchor body during insertion is important to prevent fixation failure.

Preparing the pilot hole in the bone is necessary for the anchor insertion of the existing suture anchor devices. However, there is the complexity and the hassle of manipulating the separate instruments. i.e., after the pilot hole is prepared using a separate instrument such as awl, dilator, or tapper, these instruments are removed. Then the insertion position of the suture anchor is required to be adjusted to the position and axis of the prepared pilot hole.

There are frequent cases in which it is difficult to view the surgical field due to bleeding or soft tissue swelling during arthroscopic surgery. In such a case, it becomes more difficult to insert the suture anchor into the prepared pilot hole by adjusting the position and axis of the suture anchor, which causes a delay in operating time. If the operation time is delayed during arthroscopic surgery, it becomes more difficult to secure a surgical field of view due to bleeding and soft tissue swelling. Therefore, the development of an anchor device that simplifies the surgical procedure will be useful for shortening the operation time.

As a conventional technology, "CANNULA DRIVER AND SUTURE ANCHOR KIT" is disclosed in Korean Patent No. 10-1700666 (published on Feb. 1, 2017).

A cannula driver, according to the conventional technology capable of fastening the suture anchor to a borehole in the process of forming the borehole for fixing soft tissue to a bone, includes a striker having a tapered tip provided at an end thereof such that the tip drills the borehole, the striker allowing the suture anchor to be coupled thereto such that the tip is exposed to the outside; and a guide member allowing the striker to be inserted thereto and press-fitting the suture anchor by moving the striker backward.

However, in the cannula driver according, to the conventional technology, after a hole is formed in a bone by using the striker having the tip for drilling, the suture anchor is press-fitted to the bone while the striker is moved backward. Accordingly, the guide member having a complex structure for moving the striker forward and backward is required. The striker is configured to protrude by passing through the suture anchor along a center axis thereof and has a structural problem in that the diameter of the formed hole is inevitably much smaller than the diameter of the suture anchor. Furthermore, while the suture anchor is exposed to the outside without guidance, the suture anchor is inserted into the hole, so that the suture anchor may be damaged or broken during the insertion thereof.

DISCLOSURE

Technical Problem

The present disclosure has been made keeping in mind the above problems occurring in the prior art and is intended to propose a perforator-integral suture anchor device, which may form a pilot hole in a bone without using separate instruments and may simultaneously insert and fix a suture anchor into the bone while the pilot hole is forming.

Also, the present disclosure is intended to propose a perforator-integral suture anchor device, which may form a pilot hole having the same size as or a size smaller than the size of the diameter of the suture anchor.

Furthermore, the present disclosure is intended to propose a perforator-integral suture anchor device, in which in the process of the suture anchor insertion, guide arms of an anchor driver may be coupled to an outer surface of the suture anchor and support and protect the suture anchor to reduce the possibility that the suture anchor is damaged or broken by a bone tissue.

Technical Solution

To accomplish the above objectives, a perforator-integral suture anchor device according to the present disclosure includes: a suture anchor having threads formed on an outer circumferential surface thereof; and an anchor driver capable of pressing and rotating the suture anchor such that the suture anchor is inserted and fixed into the bone, wherein the anchor driver comprises a plurality of guide arms having a length longer than the length of the suture anchor and protruding forward by being spaced apart from each other relative to a central axis of the anchor driver, and a perforating tip formed at a front end of each of the guide arms such that the perforating tip forms the pilot hole in the bone in contact therewith when pressed and rotated, and the suture anchor comprises a plurality of female coupling grooves recessed on an outer surface of the suture anchor in a longitudinal direction thereof and coupled to the plurality of guide arms such that the suture anchor is inserted and supported inside the plurality of guide arms along with longitudinal directions thereof and rotates integrally with the anchor driver.

An outer diameter defined by the plurality of guide arms may have the same size as or a size smaller than a size of the outer diameter of each of the threads of the suture anchor.

The guide arm may include two guide arms provided at positions opposite to each other relative to the central axis. The female coupling grooves of the suture anchor may be configured as two female coupling grooves to correspond to the two guide arms.

The suture anchor may have an eyelet formed through a side surface where the sutures pass through the eyelet, and the eyelet is formed in a direction crossing directions of the two female coupling grooves.

The suture anchor may have through-holes formed in a side surface where bone tissue is integrated into the suture anchor, the through-hole being formed in a direction crossing directions of the two female coupling grooves.

In addition, the perforator-integral suture anchor device, according to the present disclosure, includes: a suture anchor having threads formed on an outer circumferential surface thereof; guide arms supporting the suture anchor such that the suture anchor rotates integrally with the guide arms on a central axis of the suture anchor; when the anchor driver is pressed and rotated, a perforating tip formed at the front end of each of the guide arms protruding to a front side of the suture anchor forming a pilot hole in the bone, wherein at the same time, the suture anchor is inserted and fixed into the bone; and an anchor driver moving backward along a longitudinal direction thereof and being removed from the suture anchor fixed into the bone.

The suture anchor may be made of PEEK (polyetheretherketone), bioabsorbable, or biocomposite material.

Advantageous Effects

Due to the configuration described above, the perforator-integral suture anchor device, according to the present disclosure, may form a pilot hole in a bone and simultaneously insert and fix the suture anchor into the bone without using the separates instruments and the readjusting process of the insertion position of the suture anchor according to the position and axis of the pilot hole; therefore it can simplify the surgical procedure and a procedure instrument, thereby reducing operating time.

Also, the perforator-integral suture anchor device, according to the present disclosure, may form the pilot hole having the same size as or a size smaller than the size of the diameter of the suture anchor through the adjustment of the thickness of the guide arm according to the need of a user.

Furthermore, in the perforator-integral suture anchor device, according to the present disclosure, the guide arm may support the outer surface of the suture anchor, thereby reducing a failure rate to the fixing of the suture anchor due to the damage or breaking of the body of the suture anchor occurring in the process of the suture anchor insertion.

BEST MODE

A perforator-integral suture anchor device may include: a suture anchor having threads formed on an outer circumferential surface thereof, and an anchor driver capable of pressing and rotating the suture anchor such that the suture anchor is inserted and fixed into the bone, wherein the anchor driver may include a plurality of guide arms having a length longer than a length of the suture anchor and protruding forward by being spaced apart from each other relative to a central axis of the anchor driver, and a perforating tip formed at a front end of each of the guide arms such that the perforating tip forms the pilot hole in the bone in contact with when the anchor driver is pressed and rotated, and the suture anchor may include a plurality of female coupling grooves recessed on an outer surface of the suture anchor in a longitudinal direction thereof and coupled to the plurality of guide arms such that the suture anchor is inserted and supported inside the plurality of guide arms along with longitudinal directions thereof and rotates integrally with the anchor driver.

MODE FOR INVENTION

Hereinbelow, a perforator-integral suture anchor device according to the present disclosure will be described further in detail with reference to an embodiment illustrated in the accompanying drawings.

Figure 1:
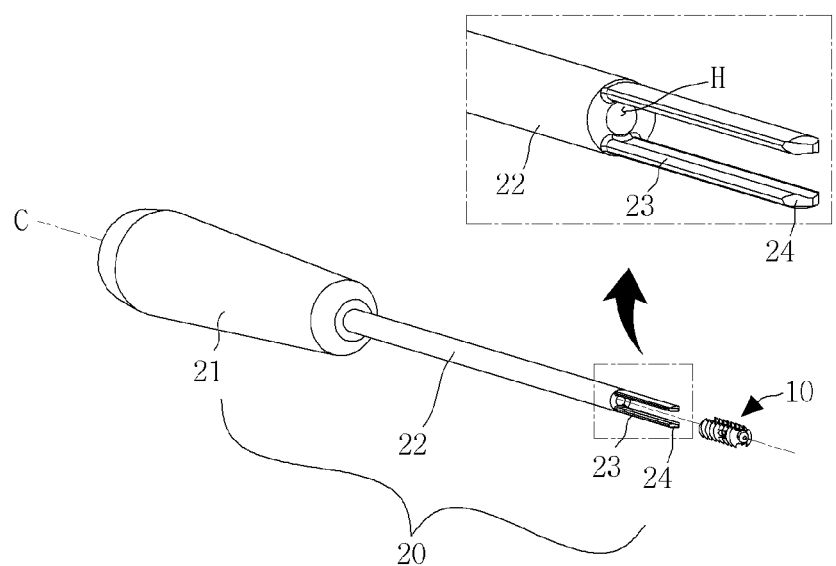
FIG. 1 is an exploded perspective view of a perforator-integral suture anchor device according to an embodiment of the present disclosure.
Figure 2:
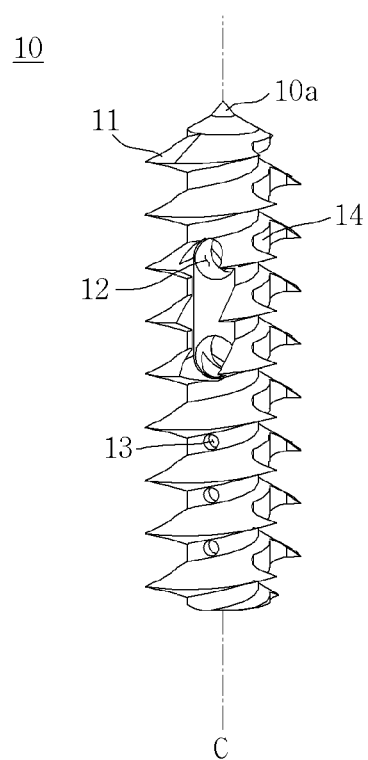
FIG. 2 is a side view of a suture anchor according to the embodiment of the present disclosure.
Figure 3:
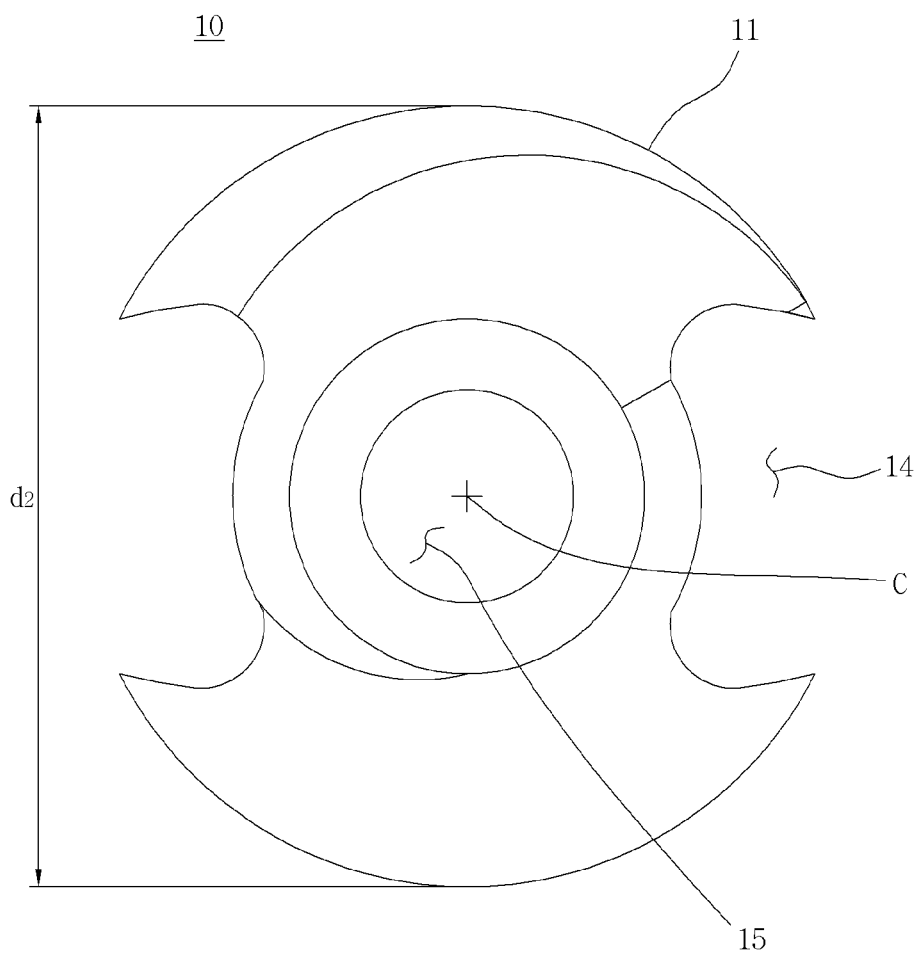
FIG. 3 is a front view of the suture anchor according to the embodiment of the present disclosure.
Figure 4:
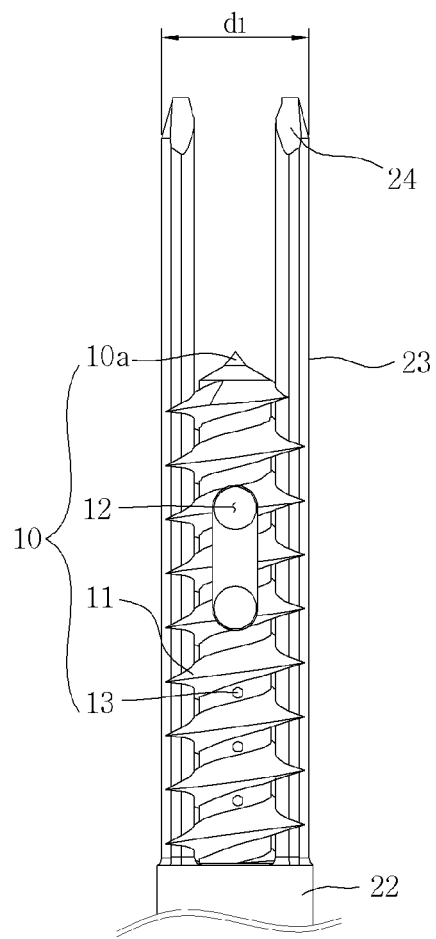
FIG. 4 is a side view of combined main parts of the perforator-integral suture anchor device according to the embodiment of the present disclosure.
Figure 5:
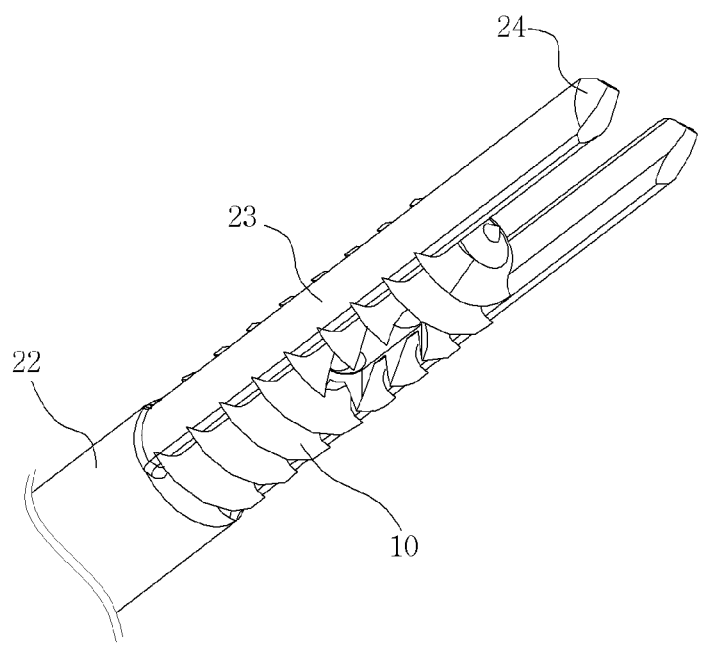
FIG. 5 is a perspective view of the combined main parts of the perforator-integral suture anchor device according to the embodiment of the present disclosure.

FIG. 1 is an exploded perspective view of the perforator-integral suture anchor device according to the embodiment of the present disclosure; FIG. 2 is a side view of a suture anchor according to the embodiment of the present disclosure; FIG. 3 is a front view of the suture anchor according to the embodiment of the present disclosure; and FIGS. 4 and 5 are a side view and a perspective view, respectively, of combined main parts of the perforator-integral suture anchor device according to the embodiment of the present disclosure.

Referring to FIGS. 1 to 5, the perforator-integral suture anchor device according to the embodiment of the present disclosure may include the suture anchor 10 and an anchor driver 20.

The suture anchor 10 may be configured to be inserted and fixed into the bone. In the embodiment of the present disclosure, the suture anchor 10 may be configured as a cylindrical body having a predetermined length and may have threads 11, eyelets 12, through-holes 13, a female coupling groove 14, and an anchor center hole 15 which are formed in the cylindrical body.

Each thread 11 may be configured by protruding by a predetermined height from the outer circumferential surface of the suture anchor 10 such that the thread has a predetermined outer diameter d2.

Due to the configuration of the threads 11, when the suture anchor 10 is pressed downward and rotated by the anchor driver 20, the protruding threads may penetrate the inner surface of the pilot hole in the bone, so the suture anchor 10 may be inserted and fixed into the bone.

Each of the eyelets 12 may be a component allowing the sutures to be attached to the suture anchor 10 and may be formed at a side surface of the suture anchor 10 such that the sutures pass through the eyelet.

The suture passing through the eyelet 12 of the suture anchor 10 may pass through the anchor center hole 15 of the suture anchor 10 and may be withdrawn to the rear end of the suture anchor 10. As illustrated in FIG. 1, the sutures are withdrawn to the rear end of the suture anchor 10 may pass through a driver center hole H formed through the anchor driver 20 in a longitudinal direction along with the central axis C of the anchor driver, and the sutures may be withdrawn to the outside of a rear end of a driver head 21.

Each of the through-holes 13 may allow bone tissue to be integrated into the anchor center hole 15 to facilitate the bonding of the bone tissue with the material of the suture anchor 10 and may be configured to function to facilitate the mounting of the suture anchor 10 to a bone. The through-hole 13 may be formed at a side surface of the suture anchor 10 at a position where the through-hole 13 does not overlap the eyelet 12.

The female coupling groove 14 may include a plurality of female coupling grooves 14 recessed on the outer surface of the suture anchor in a longitudinal direction thereof and coupled to the plurality of guide arms such that the suture anchor is inserted and supported inside the plurality of guide arms 23 to be described later along with longitudinal directions thereof and rotates integrally with the anchor driver 20.

In the embodiment of the present disclosure, the female coupling groove 14 may include two female coupling grooves to correspond to the guide arms 23 to be described later. The eyelets 12 may be formed in directions crossing directions of the two female coupling grooves 14, so the female coupling grooves 14 and the eyelets 12 may be configured to not interfere with each other.

It may be advantageous to have the suture anchor 10 that the suture anchor 10 has a pointed tip 10a such that the suture anchor 10 is penetrating through easily the bone. However, the shape of the pointed tip 10a of the suture anchor 10 may not be limited to this but may be changed to different shapes.

The anchor driver 20 may be configured to simultaneously insert and fix the suture anchor 10 into the bone while forming the pilot hole in the bone by pressing and rotating the anchor driver. In the embodiment of the present disclosure, the anchor driver 20 may include the driver head 21, a shaft 22, the plurality of guide arms 23, and a perforating tip 24.

The driver head 21 may be configured to be pressed and rotated by an external force. In the embodiment of the present disclosure, the driver head may be configured to have a shape of a handle that a user can easily press and rotate by gripping the handle with the user's hand.

The shaft 22 may have a predetermined length such that the suture anchor 10 is supported at a position spaced apart by a predetermined distance from the driver head 21, and may be configured to be coupled to the driver head 21 on the central axis C thereof such that the shaft 22 rotates integrally with the driver head 21.

Each of the plurality of guide arms 23 may have a length longer than the suture anchor 10, and may be configured by protruding from a front end of the shaft 22 and being spaced apart from each other relative to the central axis C.

In the embodiment of the present disclosure, the guide arm 23 may include two guide arms at positions opposite to each other relative to the central axis C, wherein the two guide arms 23 may be arranged parallel to each other.

The female coupling grooves 14 of the suture anchor 10 may be coupled to the plurality of guide arms 23, so the suture anchor 10 may be downward pressed and rotated integrally with the anchor driver 20. Accordingly, the part of threads 11 of the suture anchor 10 may penetrate the inner surface of the pilot hole while the perforating tips of the guide arms 23 are forming the pilot hole in the bone, so the suture anchor 10 may be inserted and fixed into the pilot hole formed by the perforating tip 24 of the guide arms 23.

Furthermore, the plurality of guide arms 23 may support the outer surface of the suture anchor 10; therefore, it can significantly reduce the possibility that the suture anchor is damaged or broken by the bone tissue in the process of the insertion of the suture anchor 10 into the bone.

Accordingly, in the case of the suture anchor 10 made of PEEK (polyetheretherketone), bioabsorbable, or biocomposite material, which has more weak material properties than metal, the outer surface of the suture anchor 10 may be sufficiently supported by the guide arms 23 having the configuration described above, so the suture anchor 10 may be inserted and fixed into the bone without being easily damaged by the bone tissue.

Meanwhile, when the anchor driver 20 is withdrawn along the longitudinal direction thereof with the suture anchor 10 inserted and fixed into the bone, the plurality of guide arms 23 may slide along the longitudinal direction of the female coupling groove 14 of the suture anchor 10 and easily removed from the fixed suture anchor 10.

The perforating tip 24 may be a component for forming the pilot hole in the bone. In the embodiment of the present disclosure, may form the perforating tip at the front end of the guide arm 23. The perforating tip 24 is configured integrally with the anchor driver 20 so that the use of separate instruments to prepare the pilot hole is not required.

When a user presses downward and rotates the driver head 21 of the anchor driver 20 exposed to the outside, the guide arm 23 and the perforating tip 24 may rotate integrally with each other. Accordingly, due to the perforating tip 24 downward pressed and rotated, it may form the pilot hole in the bone with which the perforating tip 24 is in contact.

The guide arm 23 may have a length longer than the length of the suture anchor 10. The perforating tip 24 may be formed at the front end of the guide arm 23, whereby when a user presses downward and rotates the anchor driver 20, the perforating tip 24 may first form the pilot hole in the bone while being pressed and rotated in contact with the bone. Next, the suture anchor 10 located at the rear of the perforating tip 24 may be rotated by the guide arms 23 and inserted and fixed into the pilot hole formed by the perforating tip 24.

Here, an outer diameter d1 defined by the plurality of guide arms 23 may be regarded as corresponding to the diameter of the pilot hole formed by the perforating tip 24, and may have the same size as or a size smaller than the size of the outer diameter d2 of the threads 11 of the suture anchor 10 as required.

As the outer diameter d1 defined by the plurality of guide arms 23 becomes smaller than the outer diameter d2 of the threads 11 of the suture anchor 10, the diameter of the pilot hole may become smaller than the outer diameter d2, so the fixation stability of the suture anchor 10 inserted and fixed into the bone may increase. However, the insertion of the suture anchor 10 may require more force, and each of the guide arms 23 may be required to be manufactured to have a thinner thickness, so it may not secure sufficient rigidity of the guide arm 23.

Accordingly, considering these various possibilities, the size of the outer diameter d1 defined by the plurality of guide arms 23 may be required to be determined.

As described above, in the perforator-integral suture anchor device, according to the present disclosure, the suture anchor 10 may be simultaneously inserted and fixed into the bone while the perforating tip 24 of the anchor driver 20 is forming the pilot hole. It does not require a separate instrument for the pilot hole preparation and the process of adjusting the insertion position and axis of the suture anchor 10 to the prepared pilot hole due to the organic coupling relationship between the suture anchor 10 and the anchor driver 20. Only the anchor driver 20 may be moved backward along the longitudinal direction thereof, so the anchor driver 20 may be removed from the suture anchor 10 fixed into the bone.

The perforator-integral suture anchor device described above and illustrated in the drawings may show only one embodiment for implementing the perforator-integral suture anchor device of the present disclosure and should not be construed as limiting the technical spirit of the present disclosure. The scope of protection of the present disclosure may be determined only by the matters described in the following claims. Improved and modified embodiments without departing from the gist of the present disclosure may be considered to belong to the scope of protection of the present disclosure as long as they are self-evident to those skilled in the art to which the present disclosure belongs.

DESCRIPTION OF THE REFERENCE NUMERALS IN THE DRAWINGS

10: Suture anchor
10a: Tip
11: Thread
12: Eyelet
13: Through-hole
14: Female coupling groove
15: Anchor center hole
C: Central axis
20: Anchor driver
21: Driver head
22: Shaft
23: Guide arm
24: Perforating tip
H: Driver center hole

INDUSTRIAL APPLICABILITY

According to the perforator-integral suture anchor device of the present disclosure, when tendon tears occur from its original bone attachment site due to the degeneration or injury, surgical fixation and restoration of the torn tendon by approximating the torn tendon back to the original attachment site are necessary. In this case, the suture anchor can be applied to the surgical procedure of fixing the torn tendon tissue to an original bone attachment site during arthroscopic or open surgery.

The invention claimed is:

1. A perforator-integral suture anchor device comprising:
a suture anchor having threads formed on an outer circumferential surface thereof; and
an anchor driver capable of pressing and rotating the suture anchor such that the suture anchor is inserted and fixed into a bone,
wherein the anchor driver comprises a plurality of guide arms having a length longer than a length of the suture anchor and protruding forward by being spaced apart from each other relative to a central axis of the anchor driver, and a perforating tip formed at a front end of each of the guide arms such that the perforating tip forms a pilot hole in the bone in contact therewith when pressed and rotated, and
the suture anchor comprises a plurality of female coupling grooves recessed on an outer surface of the suture anchor in a longitudinal direction thereof and coupled to the plurality of guide arms such that the suture anchor is inserted and supported inside the plurality of guide arms along with longitudinal directions thereof and rotates integrally with the anchor driver.

2. The suture anchor device of claim 1, wherein an outer diameter defined by the plurality of guide arms has the same size as or a size smaller than a size of the outer diameter of each of the threads of the suture anchor.

3. The suture anchor device of claim 2, wherein the plurality of guide arms comprise two guide arms provided at positions opposite to each other relative to the central axis, and the plurality of female coupling grooves of the suture anchor are configured as two female coupling grooves to correspond to the two guide arms.

4. The suture anchor device of claim 3, wherein the suture anchor has an eyelet formed through a side surface where a suture passes through the eyelet, and the eyelet is formed in a direction crossing directions of the two female coupling grooves.

5. The suture anchor device of claim 3, wherein the suture anchor has a through-hole formed in a side surface where bone tissue is configured to integrate into the suture anchor, the through-hole being formed in a direction crossing directions of the two female coupling grooves.

6. A perforator-integral suture anchor device comprising:
a suture anchor having threads formed on an outer circumferential surface thereof;
guide arms supporting the suture anchor such that the suture anchor rotates integrally with the guide arms on a central axis of the suture anchor;
a perforating tip formed at a front end of each of the guide arms protruding to a front side of the suture anchor forming a pilot hole in the bone, wherein at the same time, the suture anchor is inserted and fixed into the bone;
an anchor driver moving backward along a longitudinal direction thereof and being removed from the suture anchor fixed into the bone.

7. The suture anchor device of claim 1, wherein the suture anchor is made of PEEK (polyetheretherketone), bioabsorbable, or biocomposite material.

* * * * *